United States Patent [19]
Zimmermann

[11] Patent Number: 5,185,667
[45] Date of Patent: Feb. 9, 1993

[54] OMNIVIEW MOTIONLESS CAMERA ORIENTATION SYSTEM

[75] Inventor: Steven D. Zimmermann, Knoxville, Tenn.

[73] Assignee: TeleRobotics International, Inc., Knoxville, Tenn.

[21] Appl. No.: 699,366

[22] Filed: May 13, 1991

[51] Int. Cl.$^5$ .............................................. H04N 5/30
[52] U.S. Cl. ..................................... 358/209; 358/87; 358/108; 382/44
[58] Field of Search .................... 358/108, 87, 209, 85, 358/180, 229, 903, 160, 183; 359/718, 728, 364, 363; 382/44; 395/137-139

[56] References Cited

U.S. PATENT DOCUMENTS

| | | | |
|---|---|---|---|
| 4,772,942 | 9/1988 | Tuck | 358/108 |
| 5,023,725 | 6/1991 | McCutchen | 359/363 |
| 5,067,019 | 11/1991 | Juday et al. | 358/183 |
| 5,068,735 | 11/1991 | Tuchiya et al. | 358/108 |

Primary Examiner—James J. Groody
Assistant Examiner—Glenton Burgess
Attorney, Agent, or Firm—Pitts and Brittian

[57] ABSTRACT

A device for omnidirectional image viewing providing pan-and-tilt orientation, rotation, and magnification within a hemispherical field-of-view that utilizes no moving parts. The imaging device is based on the effect that the image from a fisheye lens, which produces a circular image of an entire hemispherical field-of-view, which can be mathematically corrected using high speed electronic circuitry. More specifically, an incoming fisheye image from any image acquisition source is captured in memory of the device, a transformation is performed for the viewing region of interest and viewing direction, and a corrected image is output as a video image signal for viewing, recording, or analysis. As a result, this device can accomplish the functions of pan, tilt, rotation, and zoom throughout a hemispherical field-of-view without the need for any mechanical mechanisms. The preferred embodiment of the image transformation device can provide corrected images at real-time rates, compatible with standard video equipment. The device can be used for any application where a conventional pan-and-tilt or orientation mechanism might be considered including inspection, monitoring, surveillance, and target acquisition.

11 Claims, 4 Drawing Sheets

OMNIVIEW MOTIONLESS CAMERA ORIENTATION SYSTEM

TECHNICAL FIELD

The invention relates to an apparatus, algorithm, and method for transforming a hemispherical field-of-view image into a non-distorted, normal perspective image at any orientation, rotation, and magnification within the field-of-view. The viewing direction, orientation, and magnification are controlled by either computer or remote control means. More particularly, this apparatus is the electronic equivalent of a mechanical pan, tilt, zoom, and rotation camera viewing system with no moving mechanisms.

BACKGROUND ART

Camera viewing systems are utilized in abundance for surveillance, inspection, security, and remote sensing. Remote viewing is critical for robotic manipulation tasks. Close viewing is necessary for detailed manipulation tasks while wide-angle viewing aids positioning of the robotic system to avoid collisions with the work space. The majority of these systems use either a fixed-mount camera with a limited viewing field, or they utilize mechanical pan-and-tilt platforms and mechanized zoom lenses to orient the camera and magnify its image. In the applications where orientation of the camera and magnification of its image are required, the mechanical solution is large and can subtend a significant volume making the viewing system difficult to conceal or use in close quarters. Several cameras are usually necessary to provide wide-angle viewing of the work space.

In order to provide a maximum amount of viewing coverage or subtended angle, mechanical pan/tilt mechanisms usually use motorized drives and gear mechanisms to manipulate the vertical and horizontal orientation. An example of such a device is shown in U.S. Pat. No. 4,728,839 issued to J. B. Coughlan, et al, on Mar. 1, 1988. Collisions with the working environment caused by these mechanical pan/tilt orientation mechanisms can damage both the camera and the work space and impede the remote handling operation. Simultaneously, viewing in said remote environments is extremely important to the performance of inspection and manipulation activities.

Camera viewing systems that use internal optics to provide wide viewing angles have also been developed in order to minimize the size and volume of the camera and the intrusion into the viewing area. These systems rely on the movement of either a mirror or prism to change the tilt-angle of orientation and provide mechanical rotation of the entire camera to change the pitch angle of orientation. Using this means, the size of the camera orientation system can be minimized, but "blind spots" in the center of the view result. Also, these systems typically have no means of magnifying the image and or producing multiple images from a single camera.

Accordingly, it is an object of the present invention to provide an apparatus that can provide an image of any portion of the viewing space within a hemispherical field-of-view without moving the apparatus.

It is another object of the present invention to provide horizontal orientation (pan) of the viewing direction with no moving mechanisms.

It is another object of the present invention to provide vertical orientation (tilt) of the viewing direction with no moving mechanisms.

It is another object of the present invention to provide rotational orientation (rotation) of the viewing direction with no moving mechanisms.

It is another object of the present invention to provide the ability to magnify or scale the image (zoom in and out) electronically.

It is another object of the present invention to provide electronic control of the image intensity (iris level).

It is another object of the present invention to be able to change the image intensity (iris level) without any mechanisms.

It is another object of the present invention to be able to accomplish said pan, tilt, zoom, rotation, and iris with simple inputs made by a lay person from a joystick, keyboard controller, or computer controlled means.

It is also an object of the present invention to provide accurate control of the absolute viewing direction and orientations using said input devices.

A further object of the present invention is to provide the ability to produce multiple images with different orientations and magnifications simultaneously.

Another object of the present invention is to be able to provide these images at real-time video rates, that is 30 transformed images per second, and to support various display format standards such as the National Television Standards Committee RS-170 display format.

These and other objects of the present invention will become apparent upon consideration of the drawings hereinafter in combination with a complete description thereof.

DISCLOSURE OF THE INVENTION

In accordance with the present invention, there is provided an omnidirectional viewing system that produces the equivalent of pan, tilt, zoom, and rotation within a hemispherical field-of-view with no moving parts. This device includes a means for digitizing an incoming video image signal, transforming a portion of said video image based upon operator commands, and producing one or more output images that are in correct perspective for human viewing. In one preferred embodiment, the incoming image is produced by a fisheye lens which has a hemispherical field-of-view. This hemispherical field-of-view image is captured into an electronic memory buffer. A portion of the captured image containing a region-of-interest is transformed into a perspective correct image by image processing computer means. The image processing computer provides direct mapping of the hemispherical image region-of-interest into a corrected image using an orthogonal set of transformation algorithms. The viewing orientation is designated by a command signal generated by either a human operator or computerized input. The transformed image is deposited in a second electronic memory buffer where it is then manipulated to produce the output image as requested by the command signal.

BEST MODE FOR CARRYING OUT THE INVENTION

In order to minimize the size of the camera orientation system while maintaining the ability to zoom, a camera orientation system that utilizes electronic image transformations rather than mechanisms was developed. While numerous patents on mechanical pan-and-tilt systems have been filed, no approach using strictly electronic transforms and fisheye optics has ever been successfully implemented prior to this effort. In addition, the electrooptical approach utilized in the present invention allows multiple images to be extracted from the output of a single camera. Motivation for this device came from viewing system requirements in remote handling applications where the operating envelop of the equipment is a significant constraint to task accomplishment.

Figure 1:
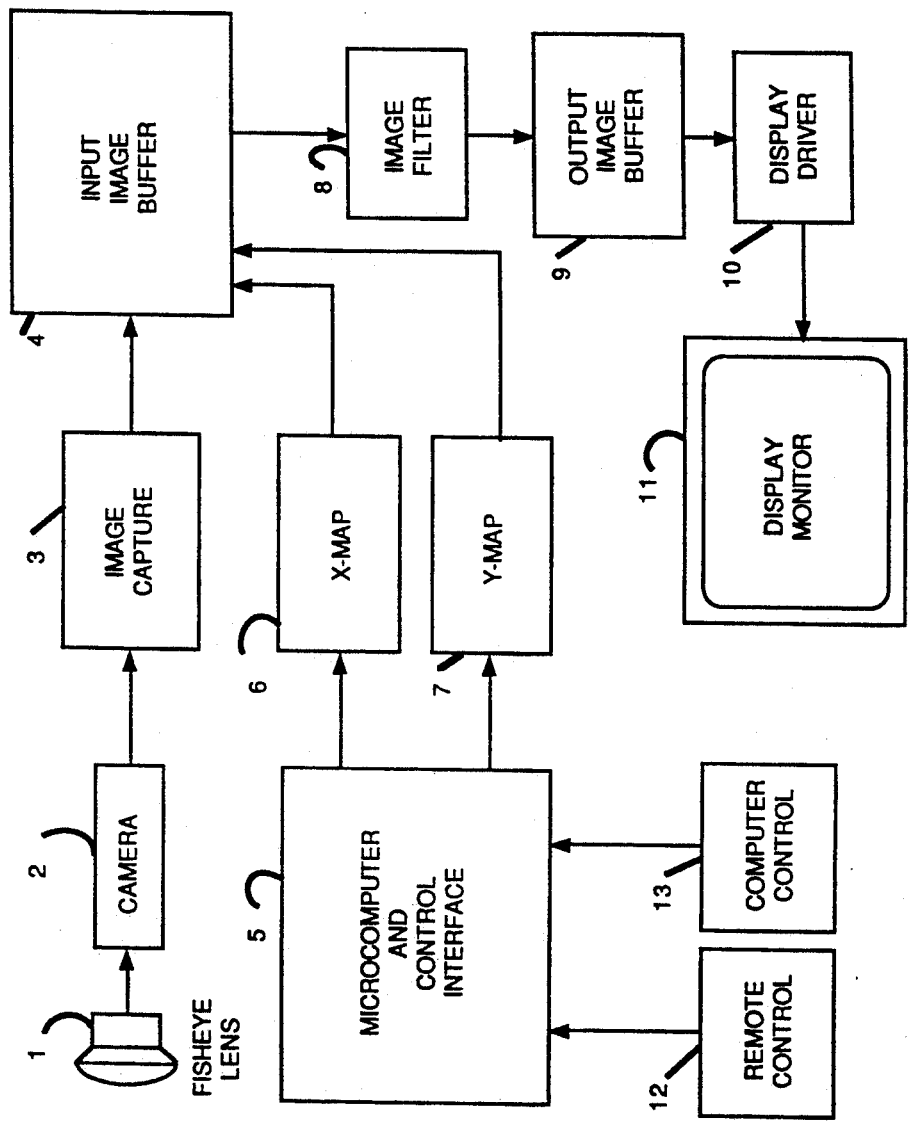
FIG. 1 shows a schematic block diagram of the present invention illustrating the major components thereof.

The principles of the present invention can be understood by reference to FIG. 1. Shown schematically at 1 is the fisheye lens that provides an image of the environment with a 180 degree field-of-view. The fisheye lens is attached to a camera 2 which converts the optical image into an electrical signal. These signals are then digitized electronically 3 and stored in an image buffer 4 within the present invention. An image processing system consisting of an X-MAP and a Y-MAP processor shown as 6 and 7, respectively, performs the two-dimensional transform mapping. The image transform processors are controlled by the microcomputer and control interface 5. The microcomputer control interface provides initialization and transform parameter calculation for the system. The control interface also determines the desired transformation coefficients based on orientation angle, magnification, rotation, and light sensitivity input from an input means such as a joystick controller 12 or computer input means 13. The transformed image is filtered by a 2-dimensional convolution filter 8 and the output of the filtered image is stored in an output image buffer 9. The output image buffer 9 is scanned out by display electronics 10 to a video display device 11 for viewing.

A range of lens types can be accommodated to support various fields of view. The lens optics 1 correspond directly with the mathematical coefficients used with the X-MAP and Y-MAP processors 6 and 7 to transform the image. The capability to pan and tilt the output image remains even though a different maximum field of view is provided with a different lens element.

The invention can be realized by proper combination of a number of optical and electronic devices. The fisheye lens 1 is exemplified by any of a series of wide angle lenses from, for example, Nikon, particularly the 8 mm F2.8. Any video source 2 and image capturing device 3 that converts the optical image into electronic memory can serve as the input for the invention such as a Videk Digital Camera interfaced with Texas Instrument's TMS 34061 integrated circuits. Input and output image buffers 4 and 9 can be constructed using Texas Instrument TMS44C251 video random access memory chips or their equivalents. The control interface can be accomplished with any of a number of microcontrollers including the Intel 80C196. The X-MAP and Y-MAP transform processors 6 and 7 and image filtering 8 can be accomplished with application specific integrated circuits or other means as will be known to persons skilled in the art. The display driver can also be accomplished with integrated circuits such as the Texas Instruments TMS34061. The output video signal can be of the NTSC RS-170, for example, compatible with most commercial television displays in the United States. Remote control 12 and computer control 13 are accomplished via readily available switches and/or computer systems that also will be well known. These components function as a system to select a portion of the input image (fisheye or wide angle) and then mathematically transform the image to provide the proper prospective for output. The keys to the success of the invention include:

(1) the entire input image need not be transformed, only the portion of interest (2) the required mathematical transform is predictable based on the lens characteristics.

Figure 3:
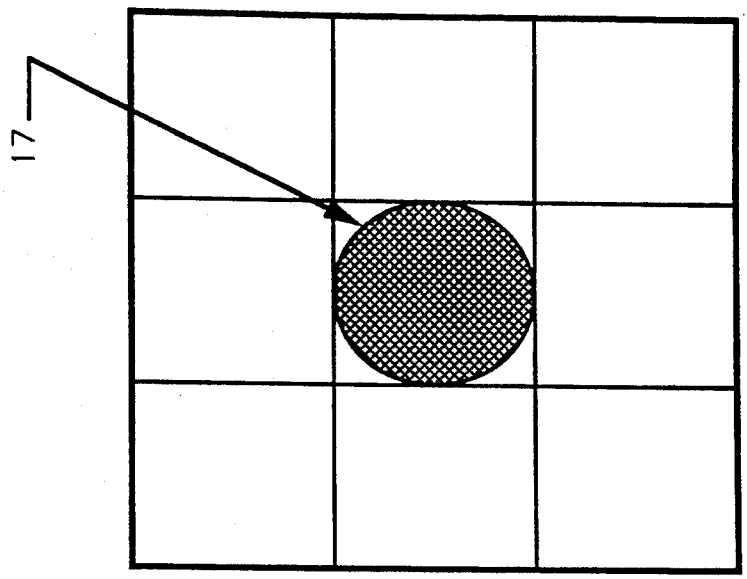
FIG. 3 is an example sketch of the output image after correction for a desired image orientation and magnification within the original image.
Figure 2:
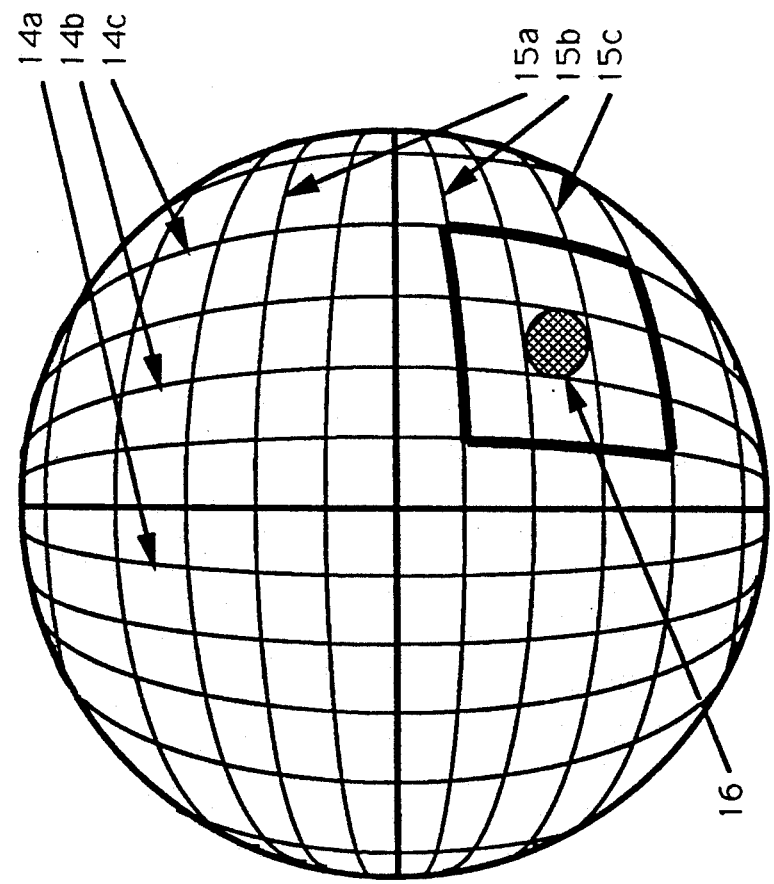
FIG. 2 is an example sketch of a typical fisheye image used as input by the present invention.

The transformation that occurs between the input memory buffer 4 and the output memory buffer 9, as controlled by the two coordinated transformation circuits 6 and 7, is better understood by looking at FIG. 2 and FIG. 3. The image shown in FIG. 2 is a pen and ink rendering of the image of a grid pattern produced by a fisheye lens. This image has a field-of-view of 180 degrees and shows the contents of the environment throughout an entire hemisphere. Notice that the resulting image in FIG. 2 is significantly distorted relative to human perception. Vertical grid lines in the environment appear in the image plane as 14a, 14b, and 14c. Horizontal grid lines in the environment appear in the image plane as 15a, 15b, and 15c. The image of an object is exemplified by 16. A portion of the image in FIG. 2 has been correct, magnified, and rotated to produce the image shown in FIG. 3. Item 17 shows the corrected representation of the object in the output display. The results shown in the image in FIG. 3 can be produced from any portion of the image of FIG. 2 using the present invention. Note the corrected perspective as demonstrated by the straightening of the grid pattern displayed in FIG. 3. In the present invention, these transformations can be performed at real-time video rates (30 times per second), compatible with commercial video standards.

The invention as described has the capability to pan and tilt the output image through the entire field of view of the lens element by changing the input means, e.g. the joystick or computer, to the controller. This allows a large area to be scanned for information as can be useful in security and surveillance applications. The image can also be rotated through 360 degrees on its axis changing the perceived vertical of the displayed image. This capability provides the ability to align the vertical image with the gravity vector to maintain a proper perspective in the image display regardless of the pan or tilt angle of the image. The invention also supports modifications in the magnification used to display the output image. This is commensurate with a zoom function that allows a change in the field of view of the output image. This function is extremely useful for inspection operations. The magnitude of zoom provided is a function of the resolution of the input camera, the resolution of the output display, the clarity of the output display, and the amount of picture element (pixel) averaging that is used in a given display. The invention supports all of these functions to provide capabilities associated with traditional mechanical pan (through 180 degrees), tilt (through 180 degrees), rotation (through 360 degrees), and zoom devices. The digital system also supports image intensity scaling that emulates the functionality of a mechanical iris by shifting the intensity of the displayed image based on commands from the user or an external computer.

The postulates and equations that follow are based on the present invention utilizing a fisheye lens as the optical element. There are two basic properties and two basic postulates that describe the perfect fisheye lens system. The first property of a fisheye lens is that the lens has a $2\pi$ steradian field-of-view and the image it produces is a circle. The second property is that all objects in the field-of-view are in focus, i.e. the perfect fisheye lens has an infinite depth-of-field. The two important postulates of the fisheye lens system (refer to FIGS. 4 and 5) are stated as follows:

Postulate 1: Azimuth angle invariability—For object points that lie in a content plane that is perpendicular to the image plane and passes through the image plane origin, all such points are mapped as image points onto the line of intersection between the image plane and the content plane, i.e. along a radial line. The azimuth angle of the image points is therefore invariant to elevation and object distance changes within the content plane.

Postulate 2: Equidistant Projection Rule—The radial distance, r, from the image plane origin along the azimuth angle containing the projection of the object point is linearly proportional to the zenith angle $\beta$, where $\beta$ is defined as the angle between a perpendicular line through the image plane origin and the line from the image plane origin to the object point. Thus the relationship:

$$r = k\beta \tag{1}$$

Figure 4:
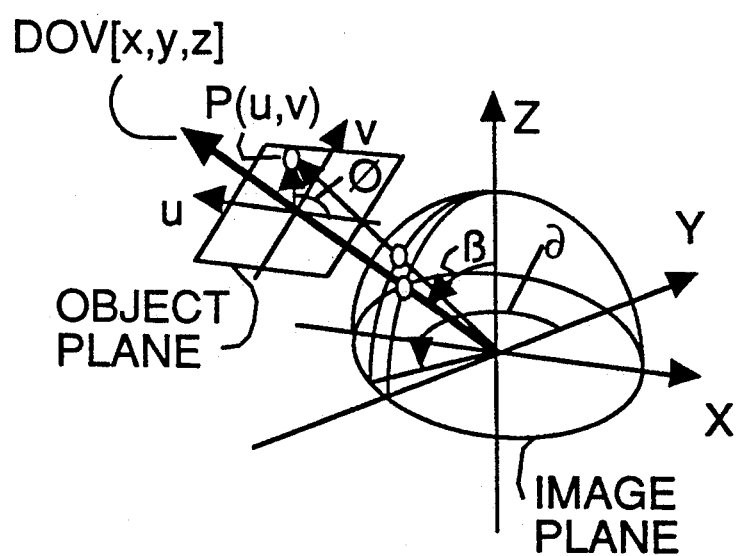
FIG. 4 is a schematic diagram of the fundamental geometry that the present invention embodies to accomplish the image transformation.

Using these properties and postulates as the foundation of the fisheye lens system, the mathematical transformation for obtaining a perspective corrected image can be determined. FIG. 4 shows the coordinate reference frames for the object plane and the image plane. The coordinates u,v describe object points within the object plane. The coordinates x,y,z describe points within the image coordinate frame of reference.

The object plane shown in FIG. 4 is a typical region of interest to determine the mapping relationship onto the image plane to properly correct the object. The direction of view vector, DOV[x,y,z], determines the zenith and azimuth angles for mapping the object plane, UV, onto the image plane, XY. The object plane is defined to be perpendicular to the vector, DOV[x,y,z].

The location of the origin of the object plane in terms of the image plane [x,y,z] in spherical coordinates is given by:

$$x = D \sin \beta \cos \partial$$

$$y = D \sin \beta \sin \partial$$

$$z = D \cos \beta \tag{2}$$

where D = scalar length from the image plane origin to the object plane origin, $\beta$ is the zenith angle, and $\partial$ is the azimuth angle in image plane spherical coordinates. The origin of object plane is represented as a vector using the components given in equation 1 as:

$$DOV[x,y,z] = [D \sin \beta \cos \partial, D \sin \beta \sin \partial, D \cos \beta] \tag{3}$$

DOV[x,y,z] is perpendicular to the object plane and its scalar magnitude D provides the distance to the object plane. By aligning the YZ plane with the direction of action of DOV[x,y,z], the azimuth angle $\partial$ becomes either 90 or 270 degrees and therefore the x component becomes zero resulting in the DOV[x,y,z] coordinates:

$$DOV[x,y,z] = [0, -D \sin \beta, D \cos \beta] \tag{4}$$

Figure 5:
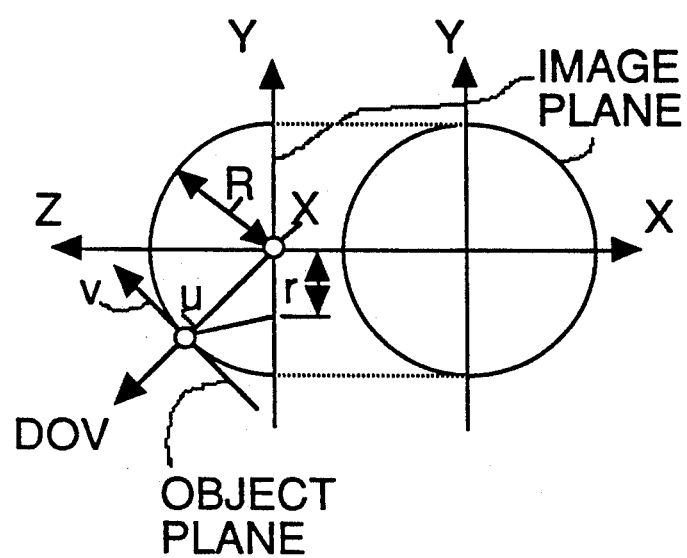
FIG. 5 is a schematic diagram demonstrating the projection of the object plane and position vector into image plane coordinates.

Referring now to FIG. 5, the object point relative to the UV plane origin in coordinates relative to the origin of the image plane is given by the following:

$$x = u$$

$$y = v \cos \beta$$

$$z = v \sin \beta \tag{5}$$

therefore, the coordinates of a point P(u,v) that lies in the object plane can be represented as a vector P[x,y,z] in image plane coordinates:

$$P[x,y,z] = [u, v \cos \beta, v \sin \beta] \tag{6}$$

where P[x,y,z] describes the position of the object point in image coordinates relative to the origin of the UV plane. The object vector O[x,y,z] that describes the object point in image coordinates is then given by:

$$O[x,y,z] = DOV[x,y,z] + P[x,y,z] \tag{7}$$

$$O[x,y,z] = [u, v \cos \beta - D \sin \beta, v \sin \beta + D \cos \beta] \tag{8}$$

Projection onto a hemisphere of radius R attached to the image plane is determined by scaling the object vector O[x,y,z] to produce a surface vector S[x,y,z]:

$$S[x,y,z] = \frac{RO[x,y,z]}{|O[x,y,z]|} \tag{9}$$

By substituting for the components of O[x,y,z] from Equation 8, the vector S[x,y,z] describing the image point mapping onto the hemisphere becomes:

$$S[x,y,z] = \frac{RO[u, (v\cos\beta - D\sin\beta), (v\sin\beta + D\cos\beta)]}{\sqrt{u^2 + (v\cos\beta - D\sin\beta)^2 + (v\sin\beta + D\cos\beta)^2}} \tag{10}$$

The denominator in Equation 10 represents the length or absolute value of the vector O[x,y,z] and can be simplified through algebraic and trigonometric manipulation to give:

$$S[x,y,z] = \frac{RO[u, (v\cos\beta - D\sin\beta), (v\sin\beta + D\cos\beta)]}{\sqrt{u^2 + v^2 + D^2}} \tag{11}$$

From equation 11, the mapping onto the two-dimensional image plane can be obtained for both x and y as:

$$x = \frac{Ru}{\sqrt{u^2 + v^2 + D^2}} \tag{12}$$

$$y = \frac{R(v\cos\beta - D\sin\beta)}{\sqrt{u^2 + v^2 + D^2}} \quad (13)$$

Additionally, the image plane center to object plane distance D can be represented in terms of the fisheye image circular radius R by the relation:

$$D = mR \quad (14)$$

where m represents the scale factor in radial units R from the image plane origin to the object plane origin. Substituting Equation 14 into Equations 12 and 13 provides a means for obtaining an effective scaling operation or magnification which can be used to provide zoom operation.

$$x = \frac{Ru}{\sqrt{u^2 + v^2 + m^2R^2}} \quad (15)$$

$$y = \frac{R(v\cos\beta - mR\sin\beta)}{\sqrt{u^2 + v^2 + m^2R^2}} \quad (16)$$

Using the equations for two-dimensional rotation of axes for both the UV object plane and the XY image plane the last two equations can be further manipulated to provide a more general set of equations that provides for rotation within the image plane and rotation within the object plane.

$$x = \frac{R[uA - vB + mR\sin\beta\sin\partial]}{\sqrt{u^2 + v^2 + m^2R^2}} \quad (17)$$

$$y = \frac{R[uC - vD - mR\sin\beta\cos\partial]}{\sqrt{u^2 + v^2 + m^2R^2}} \quad (18)$$

where:

$A = (\cos\emptyset \cos\partial - \sin\emptyset \sin\partial \cos\beta)$ $B = (\sin\emptyset \cos\partial + \cos\emptyset \sin\partial \cos\beta)$ $C = (\cos\emptyset \sin\partial + \sin\emptyset \cos\partial \cos\beta)$ $D = (\sin\emptyset \sin\partial - \cos\emptyset \cos\partial \cos\beta) \quad (19)$ and where:
R = radius of the image circle
$\beta$ = zenith angle
$\partial$ = Azimuth angle in image plane
$\emptyset$ = Object plane rotation angle
m = Magnification
u,v = object plane coordinates
x,y = image plane coordinates The Equations 17 and 18 provide a direct mapping from the UV space to the XY image space and are the fundamental mathematical result that supports the functioning of the present omnidirectional viewing system with no moving parts. By knowing the desired zenith, azimuth, and object plane rotation angles and the magnification, the locations of x and y in the imaging array can be determined. This approach provides a means to transform an image from the input video buffer to the output video buffer exactly. Also, the fisheye image system is completely symmetrical about the zenith, therefore, the vector assignments and resulting signs of various components can be chosen differently depending on the desired orientation of the object plane with respect to the image plane. In addition, these postulates and mathematical equations can be modified for various lens elements as necessary for the desired field-of-view coverage in a given application.

The input means defines the zenith angle, $\beta$, the azimuth angle, $\partial$, the object rotation, $\emptyset$, and the magnification, m. These values are substituted into Equations 19 to determine values for substitution into Equations 17 and 18. The image circle radius, R, is a fixed value that is determined by the camera lens ane element relationship. The variables u and v vary throughout the object plane determining the values for x and y in the image plane coordinates.

From the foregoing, it can be seen that a fisheye lens provides a hemispherical view that is captured by a camera. The image is then transformed into a corrected image at a desired pan, tilt, magnification, rotation, and focus based on the desired view as described by a control input. The image is then output to a television display with the perspective corrected. Accordingly, no mechanical devices are required to attain this extensive analysis and presentation of the view of an environment through 180 degrees of pan, 180 degrees of tilt, 360 degrees of rotation, and various degrees of zoom magnification.

I claim:

1. A device for providing perspective corrected views of a selected portion of a hemispherical view in a desired format that utilizes no moving parts, which comprises:

a camera imaging system for receiving optical images and for producing output signals corresponding to said optical images;

fisheye lens means attached to said camera imaging system for producing said optical images, throughout said hemispherical field-of-view, for optical conveyance to said camera imaging system;

image capture means for receiving said output signals from said camera imaging system and for digitizing said output signals from said camera imaging system;

input image memory means for receiving said digitized signals;

image transform processor means for processing said digitized signals in said input image memory means according to selected viewing angles and magnification, and for producing output transform calculation signals according to a combination of said digitized signals, said selected viewing angles and said selected magnification;

output image memory means for receiving said output signals from said image transform processor means;

input means for selecting said viewing angles and magnification;

microprocessor means for receiving said selected viewing angles and magnification from said input means and for converting said selected viewing angles and magnification for input to said image transform processor means to control said processing of said transform processor means; and output means connected to said output image memory means for recording said perspective corrected view according to said selected viewing angles and magnification.

2. The device of claim 1 wherein said output means includes image display means for providing a perspective corrected image display according to said selected viewing angle and said magnification.

3. The device of claim 1 wherein said input means further provides for input of a selected portion of said hemispherical view to said transform processor means.

4. The device of claim 1 wherein said input means further provides for input of a selected tilting of said viewing angle through 180 degrees.

5. The device of claim 1 wherein said input means further provides for input of a selected rotation of said viewing angle through 360 degrees to achieve said perspective corrected view.

6. The device of claim 1 wherein said input means further provides for input of a selected pan of said viewing angle through 180 degrees.

7. The device of claim 1 wherein said output transform calculation signals of said image transform processor means are produced in real-time at video rates.

8. The device of claim 1 wherein said input means is a user-operated manipulator switch means.

9. The device of claim 1 wherein said image transform processor means is programmed to implement the following two equations:

$$x = \frac{R\{uA - vB + mR\sin\beta\sin\partial\}}{\sqrt{u^2 + v^2 + m^2R^2}}$$

$$y = \frac{R\{uC - vD - mR\sin\beta\cos\partial\}}{\sqrt{u^2 + v^2 + m^2R^2}}$$

where:

$A = (\cos\emptyset \cos\partial - \sin\emptyset \sin\partial\cos\beta)$ $B = (\sin\emptyset \cos\partial + \cos\emptyset \sin\partial\cos\beta)$ $C = (\cos\emptyset \sin\partial + \sin\emptyset \cos\partial\cos\beta)$ $D = (\sin\emptyset \sin\partial - \cos\emptyset \cos\partial\cos\beta)$ and where:
R = radius of the image circle
$\beta$ = zenith angle
$\partial$ = Azimuth angle in image plane
$\emptyset$ = Object plane rotation angle
m = Magnification
u,v = object plane coordinates
x,y = image plane coordinates 10. A device for providing perspective corrected views of a selected portion of a hemispherical view in a desired format that utilizes no moving parts, which comprises:
   a camera imaging system for receiving optical images and for producing output signals corresponding to said optical images;
   fisheye lens means attached to said camera imaging system for producing said optical images, throughout said hemispherical field-of-view, for optical conveyance to said camera imaging system;
   image capture means for receiving said output signals from said camera imaging system and for digitizing said output signals from said camera imaging system;
   input image memory means for receiving said digitized signals;
   image transform processor means for processing said digitized signals in said input image memory means according to selected viewing angles and magnification, and for producing output signals, said selected viewing angles and said selected magnification, according to the equations;

$$x = \frac{R[uA - vB + mR\sin\beta\sin\partial]}{\sqrt{u^2 + v^2 + m^2R^2}}$$

$$y = \frac{R[uC - vD - mR\sin\beta\cos\partial]}{\sqrt{u^2 + v^2 + m^2R^2}}$$

where:

$A = (\cos\emptyset \cos\partial - \sin\emptyset \sin\partial\cos\beta)$ $B = (\sin\emptyset \cos\partial + \cos\emptyset \sin\partial\cos\beta)$ $C = (\cos\emptyset \sin\partial + \sin\emptyset \cos\partial\cos\beta)$ $D = (\sin\emptyset \sin\partial - \cos\emptyset \cos\partial\cos\beta)$ and where:
R = radius of the image circle
$\beta$ = zenith angle
$\partial$ = Azimuth angle in image plane
$\emptyset$ = Object plane rotation angle
m = Magnification
u,v = object plane coordinates
x,y = image plane coordinates output image memory means for receiving said output signals from said image transform processor means;
   input means for selecting said viewing angles and magnification;
   microprocessor means for receiving said selected viewing angles and magnification from said input means and for converting said selected viewing and magnification for input to said image transform processor means to control said processing of said transform processor means; and
   output means connected to said output image means for recording said perspective corrected views according to said selected viewing angles and implementation.

11. A device for providing perspective corrected views of a selected portion of a hemispherical view in a desired format that utilizes no moving parts, which comprises:
   a camera imaging system for receiving optical images and for producing output signals corresponding to said optical images;
   fisheye lens means attached to said camera imaging system for producing said optical images, throughout said hemispherical field-of-view, for optical conveyance to said camera imaging system;
   image capture means for receiving said output signals from said camera imaging system and for digitizing said output signals from said camera imaging system;
   input image memory means for receiving said digitized signals;
   image transform processor means for processing said digitized signals in said input image memory means according to selected viewing angles and magnification, and for producing output transform calculation signals in real-time at video rates according to a combination of said digitized signals, said viewing angles and said selected magnification;
   user operated input means for selecting said viewing angles and magnification;

microprocessor means for receiving said selected viewing angles and magnification from said user operated input means and for converting said selected viewing angles and magnification for input to said image transform processor means to control said processing of said transform processor means;

output image memory means for receiving said output transform calculation signals in real-time and at video rates from said image transform processor means; and output means connected to said output image memory means for recording said perspective corrected views according to said selected viewing angles and magnification.

* * * * *